United States Patent
Ferber et al.

(10) Patent No.: US 9,439,417 B2
(45) Date of Patent: Sep. 13, 2016

(54) SILICONE ELASTOMER PRODUCT EXHIBITING A BIOCIDAL ACTIVITY

(75) Inventors: Marc Ferber, Biot (FR); Christophe Lebaron, Chalette sur Loing (FR); Franck Renauld, Epernay (FR)

(73) Assignee: SAINT GOBAIN PERFORMANCE PLASTICS FRANCE, Charny (FR)

(*) Notice: Subject to any disclaimer, the term of this patent is extended or adjusted under 35 U.S.C. 154(b) by 694 days.

(21) Appl. No.: 13/000,410

(22) PCT Filed: Jun. 22, 2009

(86) PCT No.: PCT/FR2009/051183
§ 371 (c)(1),
(2), (4) Date: Mar. 23, 2011

(87) PCT Pub. No.: WO2010/007284
PCT Pub. Date: Jan. 21, 2010

(65) Prior Publication Data
US 2011/0165246 A1    Jul. 7, 2011

(30) Foreign Application Priority Data
Jun. 24, 2008 (FR) ................................ 08 54159

(51) Int. Cl.
| | |
|---|---|
| *A01N 25/00* | (2006.01) |
| *A01N 55/10* | (2006.01) |
| *A01P 1/00* | (2006.01) |
| *A61K 9/14* | (2006.01) |
| *A61K 31/74* | (2006.01) |
| *A01N 33/12* | (2006.01) |
| *A01N 55/00* | (2006.01) |

(52) U.S. Cl.
CPC ............... *A01N 33/12* (2013.01); *A01N 55/00* (2013.01)

(58) Field of Classification Search
CPC .............................. A01N 33/12; A01N 25/34
See application file for complete search history.

(56) References Cited

U.S. PATENT DOCUMENTS

| | | | | |
|---|---|---|---|---|
| 4,911,899 | A * | 3/1990 | Hagiwara et al. | 423/700 |
| 5,723,420 | A * | 3/1998 | Wei et al. | 510/101 |
| 6,146,688 | A | 11/2000 | Morgan et al. | |
| 6,572,926 | B1 | 6/2003 | Morgan et al. | |
| 2002/0193879 | A1* | 12/2002 | Seder et al. | 623/9 |
| 2005/0008613 | A1* | 1/2005 | Peterson et al. | 424/78.27 |
| 2007/0255004 | A1 | 11/2007 | Lohrmann et al. | |

FOREIGN PATENT DOCUMENTS

| | | | | |
|---|---|---|---|---|
| EP | 1 217 052 | A2 | 6/2002 | |
| EP | 1217052 | A2 * | 6/2002 | ............... C09J 4/00 |
| JP | 2000-088153 | | 3/2000 | |
| JP | 2001-526310 | | 12/2001 | |
| JP | 2002-178452 | | 6/2002 | |
| JP | 2004-352617 | | 12/2004 | |
| WO | 99/32157 | | 7/1999 | |
| WO | WO 99/32157 | | 7/1999 | |
| WO | WO 2004/105687 | A2 | 12/2004 | |
| WO | WO 2006/102367 | A1 | 9/2006 | |
| WO | WO 2007/124855 | A2 | 11/2007 | |

OTHER PUBLICATIONS

International Search Report issued May 4, 2010, in Patent Application No. PCT/FR2009/051183.
"Material Safety Data Sheet", The Clay Minerals Society, http://www.agry.purdue.edu/cjohnston/sourceclays/SWy-2.pdf   XP 2517820, May 2, 2001, pp. 1-4.
Hui Li, et al., "Geochemical Modulation of Pesticide Sorption on Smectite Clay", Environmental Science Technology, vol. 38 No. 20, XP 2517821, 2004, pp. 5393-5399.

* cited by examiner

*Primary Examiner* — Kyle Purdy
(74) *Attorney, Agent, or Firm* — Oblon, McClelland, Maier & Neustadt, L.L.P.

(57) ABSTRACT

The present invention relates to an antimicrobial product obtained from a silicone-based system exhibiting a biocidal activity on its surface, said system comprising a silicone elastomer matrix and a mineral filler of particles chosen from the group of the silicas or aluminosilicates, for example zeolites or bentonites, said particles being dispersed in said matrix and comprising, grafted to their surface, molecules of the alkylsilane type incorporating at least one quaternary ammonium functional group.

20 Claims, No Drawings

SILICONE ELASTOMER PRODUCT EXHIBITING A BIOCIDAL ACTIVITY

This application is a National Stage of PCT/FR09/051183 filed Jun. 22, 2009 and claims the benefit of FR 08 54159 filed Jun. 24, 2008.

The present invention relates to the field of antimicrobial and biocompatible products, in particular for food applications. More particularly, the invention relates to a product exhibiting an antimicrobial biocidal activity at its surface which is obtained from a silicone-based organosilicon system.

The aim of the present invention is to provide products exhibiting an antimicrobial activity but which are compatible in particular with use in the field of food. One of the possible examples of the use of such a product is in particular the preparation of tubes for the delivery of liquid foods, such as coffee, fruit juices, soups, and the like.

Thus, by way of example, if a tube used to deliver a liquid food is used in a dispensing device, in the absence of any antimicrobial treatment of the tube, it is necessary to change it very frequently in order to avoid any risk of food poisoning related to the growth of bacterial or mold colonies first at the surface of the internal aperture and then in the stagnant liquid. Such changes are very expensive and it is easily seen that the slightest oversight may have very serious health consequences.

The use of different polymeric matrices for the preparation of antimicrobial food tubes is already well known: food tubes obtained with matrices of different natures, for example of PVC, TPE, TPU or silicone, are thus identified. Generally, it is currently commonplace to disperse, in these matrices, an agent exhibiting an antimicrobial action, generally based on silver salts, in order to limit in particular the growth of bacteria, such as *Pseumodas aeruginosa* or *Escherichia coli*, which are the most dangerous to human health.

More recently, it has been found that it is possible to replace the silver with other molecules having an antimicrobial effect which is just as effective but which are less expensive. Mention may in particular be made of quaternary ammonium derivatives, the biocidal action of which could be demonstrated, for example, in patent application WO 99/32157.

More recently still, a description has also been given, in U.S. Pat. No. 6,572,926 B1, of the use of quaternary ammonium salts also exhibiting an ending of the alkoxyalkylsilane type capable of polymerizing, according to an interpenetrating network, into a polymer matrix of the abovementioned type.

These solutions make it possible to solve the problem set out above of preventing or at least of greatly restricting the growth of bacterial colonies. However, they exhibit the major disadvantage that a portion of the biocidal molecules are continually released into the aperture of the tube and into the liquid circulating therein. Even if the amount of material thus released proves to be minimal, it constitutes another contamination of the liquid foods, the consequences of which are poorly known even today.

The aim of the present invention is thus to provide a product obtained from a novel material having a biocidal activity which makes it possible to greatly restrict the growth of bacteria and other microorganisms at its surface but which is inert with regard to the external environment, that is to say the biocidal constituent of which is not capable of "sweating" and of being released at the surface of the material and into the external environment.

Such an aim was achieved according to the invention by virtue of the use of the product which is a subject matter of the present invention.

More specifically, the present invention relates to an antimicrobial product obtained from a silicone-based system exhibiting a biocidal activity on its surface, said system comprising a silicone elastomer matrix and a mineral filler of particles chosen from the group of the silicas, zeolites or bentonites, or more generally aluminosilicates, said particles being dispersed in said matrix and comprising, grafted to their surface, molecules of the alkylsilane type incorporating at least one quaternary ammonium functional group.

Preferably, the grafted alkylsilane molecules are obtained from at least one precursor of the type:

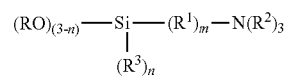

in which:
m is an integer varying between 1 inclusive and 10 inclusive,
n is equal to 0, 1 or 2,
R represents a linear alkyl chain of the $CH_3-(CH_2)_w$- type, in which w is between 0 and 5, or an isomeric branched form of said linear chain,
$R^1$ is a hydrocarbon chain optionally comprising alcohol and/or ether, epoxy or aryl functional groups,
the $R^2$ groups, which are identical or different on the same precursor, each represent a linear alkyl chain of the $(CH_2)_z-CH_3$ type, with z between 1 and 30, or an isomeric branched form of said linear chain,
$R^3$ is a linear alkyl chain $CH_3-(CH_2)_w$, w being between 0 and 5, or an isomeric branched form of said linear chain or also another alkylsilane group.

The precursors in which m=1, n=0, w=0, 1 or 2, $R^1$ represents a linear alkyl of the $(CH_2)_y$ type, y being between 1 and 10, preferably between 1 and 5, or an isomeric branched form of said linear form, and in which, preferably and for at least one of the $R^2$ groups, z is greater than 15 are particularly preferred according to the invention.

It is clearly understood that all the combinations are possible according to the invention as regards the values set out above, whether within the broad ranges or the preferred ranges of values or even the values themselves. All the combinations of the values, in particular of m, n, w, $R^1$, $R^2$ and z, are envisaged and should be regarded as included by this simple reference in the present description, even if they are not explicitly described, in order not to unnecessarily expand the present description.

According to a favored embodiment, the grafted alkylsilane molecules are obtained from a precursor of formula:

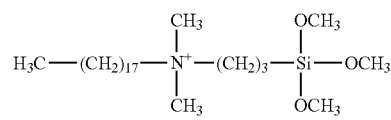

According to the invention, the mean size of the particles constituting the mineral filler is advantageously between 0.01 micron and 500 microns, preferably between 0.1 micron and 200 microns.

Said particles can in particular be composed of an amorphous material, preferably an amorphous silica, the specific surface of which is between 10 and 1000 m²/g, preferably between 50 and 500 m²/g.

According to a preferred form, the ratio by weight of the alkylsilane to the silicone elastomer matrix is less than 3%, indeed even less than 2%. According to the invention, said ratio by weight is preferably greater than 0.01%. Depending on the type and the severity of the contamination of the external environment, the ratio by weight can be brought, without departing from the context of the invention, to values of greater than 0.05% or even greater than 0.1%.

On the other hand, it has been found, by the Applicant, that greatly reduced amounts of the biocidal agent, of the order of 0.005%, indeed even less, would still bring about a very appreciable biocidal activity, provided that the agent is grafted at the surface of a filler according to the invention. Without departing from the context of the invention, such amounts, for example ratios by weight of the alkylsilane to the silicone elastomer matrix of the order of 0.005% to 0.01%, should be regarded as also coming within the scope of the present invention.

According to an example applicable in a conventional food use, the ratio by weight can ideally be between 0.01% and 0.2%.

The ratio by weight of the mineral filler to the silicone elastomer matrix can be between 0.1% and 50%, preferably between 0.5% and 20%.

The invention also relates to the use of a silicone elastomer tube as described above for the delivery of liquid foods, such as, for example coffee, fruit juices, soups or other liquid foods.

The product according to the invention is of use in the field of food but is very clearly not restricted thereto. Mention may in particular be made, as possible field of use, without this list being restricting, of any food or nonfood field in which the presence of bacteria may constitute a problem, for example as component of a silicone computer keyboard, in the manufacture of silicone touch keys, as silicone leaktight seals for health or industrial applications, in the manufacture of pipes for the circulation of gases or of condensate systems in aircraft or more generally of air systems in aircraft.

Within the meaning of the present description, "product" is understood to mean an object which can exhibit any shape in three dimensions. By way of example, mention may be made, as such products or objects, of plaques, sheets, tubes or pipes, solid or hollow spheres, or any other spatial conception.

Silicone elastomer is understood to mean any system polymerizable in three dimensions which has, as starting monomers or polymers, at least 50% of compounds having a polydimethylsiloxane chain. Examples are "peroxide catalysis" silicone elastomers, "platinum salts catalysis" silicone elastomers, polydimethylsiloxane monomers or polymers having hydrolyzable groups (examples: methoxy, ethoxy), and other crosslinkable systems known in this field.

In particular, use may be made, according to the invention, without distinction, of silicone elastomers obtained from compositions which crosslink at ambient temperature ("RTV" compositions) or at higher temperatures (high temperature vulcanizing or HTV compositions) under the effect of various types of catalysts or other crosslinking agents. The starting elastomer compositions can be chosen for crosslinking under the effect of heating or radiation, such as UV radiation or infrared radiation. According to the invention, use may also be made of more or less functionalized silicone elastomers provided in the mono-, bi- or tricomponent form.

The silicone elastomers which can be used according to the present invention are, for example, those described previously in patent application EP 1 115 364 A1.

Natural or synthetic mineral compounds, in particular of the clay, aluminosilicate or silica type, reinforcing agents, pigments, dyes or other known additives commonly used in the manufacture of silicone elastomers can be incorporated in these silicone elastomers.

Biocidal is understood to mean any effect intended to destroy, repel or render inoffensive, by lethal or nonlethal action, harmful organisms, to prevent the action thereof or to combat them.

By way of examples, the harmful organisms, also denoted in the present description under the generic terms microbe or microbial agent, are generally unicellular organisms, such as bacteria, yeast and others. Use may in particular be made, according to the invention, of the biocides described in U.S. Pat. No. 6,572,926 B1.

Surface is understood to mean any part of the silicone elastomer being in contact with its external environment, which can be gaseous, solid or liquid, in particular aqueous.

According to the invention, products based on a silicone elastomer having surface biocidal properties can advantageously be prepared by incorporation, in the silicone elastomer and preferably before the crosslinking thereof, of natural or synthetic mineral fillers exhibiting biocidal properties as described above. The final products are obtained by crosslinking the noncrosslinked elastomer incorporating such fillers having biocidal activity, according to the three-dimensional shape desired, by conventional extrusion, molding, coextrusion or injection molding processes or any other process known in this field.

According to one possible implementation, the extrusion of a noncrosslinked silicone elastomer comprising said filler as described above makes it possible to obtain, after crosslinking, a hollow tube, the internal and external surfaces of which exhibit a biocidal activity by contact.

According to another possible implementation, the coextrusion of a noncrosslinked silicone elastomer comprising said filler with another noncrosslinked silicone elastomer but without said filler makes it possible to obtain a tube, only the internal or external surface of which exhibits a biocidal activity, according to the type of coextrusion used.

According to the invention, the filler exhibiting a biocidal activity thus forms an integral part of the elastomer and in particular cannot migrate to the surface of the product in order to be released there into the external environment. Such properties thus allow them to be used in industries or activities sensitive to contamination, in particular food industries or activities.

The examples which follow, which are nonlimiting of the invention, are given with the aim of illustrating the advantages of the product described above.

EXAMPLES

A—Synthesis of the Mineral Fillers

Various fillers were synthesized in a first step:
a) A reference filler composed solely of amorphous silicon dioxide particles sold under the reference Cab-O-Sil M5® by Cabot.

b) A filler 1 obtained under the following conditions: 30 grams of amorphous silica Cab-O-Sil M5® are introduced into a fluidized bed. 10 grams of (trimethoxysilyl)propyldimethyloctadecylammonium chloride EPA 34292-1—CAS 27668-52-6—EINECS 248-595-8 (72% by weight in an aqueous solution) are sprayed into the fluidized bed. The expanded formula of this alkylsilane comprising a tetrafunctional (quaternary) amine functional group is as follows:

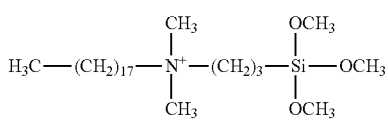

This product is currently sold under the reference AEM 5772® by Aegis Corp. The mixture obtained is left at ambient temperature for 24 hours in order to obtain complete reaction between the silica and the alkylsilane.

c) A filler 2 obtained under the same conditions as for filler 1 but by a reaction, in a fluidized bed, between 30 grams of amorphous silica Cab-O-Sil M5® and 5 grams of the 72% aqueous (trimethoxysilyl)-propyldimethyloctadecylammonium chloride solution.

d) A filler 3 obtained under the same conditions as for filler 1 but by a reaction, in a fluidized bed, between 30 grams of amorphous silica Cab-O-Sil M5® and 3 grams of the 72% aqueous (trimethoxysilyl)-propyldimethyloctadecylammonium chloride solution.

B—Measurement of the Level of Biocidal Molecules

In a second step, the level of alkylsilane which has not reacted with the silica filler (and which can potentially be released at the surface of the product) is determined was measured according to the following experimental protocol:

5 g of the grafted silica to be analyzed are introduced into a beaker. 100 grams of distilled water are introduced and the combined mixture is stirred for 1 hour, left standing for 24 hours and then centrifuged.

The supernatant is withdrawn and filtered through a 0.2 μm Millipore filter.

10 g of the filtrate collected are analyzed in colorimetry at 589 nm and 595 nm by reaction with bromophenol blue according to the following experimental protocol:

1—Establishment of a Calibration Curve:

An alkylsilane mother solution is first prepared by mixing 100 μl of a concentrated aqueous solution comprising 72% by weight of the precursor are added to 100 g of distilled water.

Various solutions are subsequently prepared, corresponding to different levels of concentrations:

9.975 ml of distilled water+25 μl of mother solution, i.e. 0.0175 mg of alkylsilane agent comprising the quaternary amine,
9.950 ml of distilled water+50 μl of mother solution, i.e. 0.0350 mg of alkylsilane agent,
9.900 ml of distilled water+100 μl of mother solution, i.e. 0.0750 mg of alkylsilane agent,
9.750 ml of distilled water+250 μl of mother solution, i.e. 0.1750 mg of alkylsilane agent,
10 ml of distilled water+0 μl of mother solution, i.e. 0 mg of alkylsilane agent.

A bromophenol blue solution is also prepared in the following way: 50 mg of bromophenol blue are dissolved in 150 ml of distilled water and the solution is used within 24 hours.

The absorption at 589 nm and 595 nm, corresponding to the absorption wavelengths of the bromophenol blue-quaternary amine complexes, is measured in order to establish the calibration curve which makes possible the measurement of the concentration of quaternary ammonium chloride (table 1):

TABLE 1

| λ (nm) | Concentration (mg) | | | | |
|---|---|---|---|---|---|
|  | 0 | 0.0175 | 0.0350 | 0.0700 | 0.1750 |
| 589 | 0.233 | 0.229 | 0.226 | 0.223 | 0.210 |
| 595 | 0.231 | 0.227 | 0.225 | 0.222 | 0.212 |

2—Assaying of the Filtrates:

50 μl of the bromophenol blue solution are added to 10 g of the solutions to be analyzed and the combined mixture is stirred for a few minutes and introduced into a colorimeter. The results obtained are combined in table 2:

TABLE 2

| λ (nm) | Sample | | | |
|---|---|---|---|---|
|  | Reference | Filler 3 | Filler 2 | Filler 1 |
| 589 | 0.233 | 0.233 | 0.234 | 0.234 |
| 595 | 0.231 | 0.232 | 0.232 | 0.232 |

It can thus be established that the alkylsilanes in their entirety are grafted to the various silica fillers (filler 1, 2 or 3) and that the biocidal active principle thus cannot be "released" at the surface of the product, in accordance with the present invention.

The same experimental protocol was again carried out but with extraction of the silica fillers with hexane, that is to say that the distilled water was replaced during extraction with 100 g of n-hexane. The experimental results show the same properties of grafting of the biocidal alkylsilane to the silica.

D—Preparation of the Products According to the Invention

The fillers were incorporated according to the invention in a silicone elastomer matrix. The various mixtures are produced using, as matrix, a silicone base sold by Rhodia Silicone under the reference Rhodorsil MF 960 U. The silicone base is vulcanized by the use of a product sold under the reference Perkadox PD 50s®, the vulcanizing agent of which is di(2,4-dichlorobenzoyl) peroxide.

The proportions by weight (base 100 for the silicone base) of the various constituents used for the ten examples carried out are combined in table 3 below.

TABLE 3

|  | Ex. 1 | Ex. 2 | Ex. 3 | Ex. 4 | Ex. 5 | Ex. 6 | Ex. 7 | Ex. 8 | Ex. 9 | Ex. 10: Control |
|---|---|---|---|---|---|---|---|---|---|---|
| Silicone base | 100 | 100 | 100 | 100 | 100 | 100 | 100 | 100 | 100 | 100 |
| Perkadox Pd 50s | 1.25 | 1.25 | 1.25 | 1.25 | 1.25 | 1 | 1.3 | 1.25 | 1.25 | 1.25 |
| Filler 2 | 2 | 5 | 10 | — | — | — | — | — | — | — |
| Filler 1 | — | — | — | 2 | 5 | 10 | — | — | — | — |
| Filler 3 | — | — | — | — | — | — | 2 | 5 | 10 | — |

More specifically, the protocol used is as follows:
1) heating the silicone base with three successive passes over vertical cylinders,
2) introducing the filler (1, 2 or 3),
3) introducing the Perkadox PD 50s® vulcanizing system,
4) adjusting to a thickness of 0.5 cm for cutting out plaques and vulcanizing,
5) vulcanizing at 100° C. for 10 minutes in a molding machine, closing at 250 bar and then stoving at 200° C. for 4 hours in order to obtain a crosslinked silicone plaque.

E—Biocidal Activity

The biocidal activity of Ex. 1 to 9 and of the control product was determined according to standard JIS Z 2801-2000. The bacterial strain used is *Escherichia coli*.

According to this standard and the conventional protocol, the biocidal activity of the products obtained from the compositions according to examples 1 to 9 is measured by the difference between the $Log_{10}$ of the number of bacterial colonies growing (also known as CFU in the field) on the treated product and the $Log_{10}$, of the number of bacterial colonies growing in the absence of any product after 24 hours.

The results obtained for the products according to examples 1 to 9, by comparison with the blank (without product) and the control product (without filler), are summarized in table 4.

TABLE 4

| Example | Filler | Filler/matrix (% by weight) | Alkylsil./matrix (% by weight) | $Log_{10}$ CFU | $Log_{10}$ CFU reduction | Activity (%) |
|---|---|---|---|---|---|---|
| Blank | — | — | — | 5.87 | — | — |
| Control | none | 0 | 0 | 4.81 | 1.06 | |
| Ex. 1 | 2 | 2 | 0.21 | 0.00 | 5.87 | >99.9 |
| Ex. 2 | 2 | 5 | 0.51 | 0.00 | 5.87 | >99.9 |
| Ex. 3 | 2 | 10 | 1.03 | 0.00 | 5.87 | >99.9 |
| Ex. 4 | 1 | 2 | 0.36 | 0.00 | 5.87 | >99.9 |
| Ex. 5 | 1 | 5 | 0.90 | 0.00 | 5.87 | >99.9 |
| Ex. 6 | 1 | 10 | 1.80 | 4.55 | 1.32 | |
| Ex. 7 | 3 | 2 | 0.13 | 0.00 | 5.87 | >99.9 |
| Ex. 8 | 3 | 5 | 0.33 | 0.00 | 5.87 | >99.9 |
| Ex. 9 | 3 | 10 | 0.66 | 0.00 | 5.87 | >99.9 |

It is noticed that the products obtained according to the invention make it possible to reduce *E. coli* bacterial growth in a proportion of approximately 100%, thus demonstrating a very high biocidal activity of the systems according to the invention. Surprisingly, it is also noticed that an excessively high proportion of the alkylsilane biocidal agent comprising a quaternary amine functional group results in an appreciable decrease in the antibacterial activity of the product.

F—Study of the Biocidal Activity at Very Low Concentrations of the Alkylsilane

Other products according to the invention were prepared on the model of examples 1 to 9 above. However, the samples were obtained from fillers 1', 2' and 3' according to a method similar to that described above but in which use was made this time of a solution of (trimethoxysilyl)propyldimethyloctadecylammonium chloride diluted at 5% by weight in an aqueous solution.

More specifically:
the filler 1' is obtained by spraying, in a fluidized bed, 30 grams of amorphous silica Cab-O-Sil M5® with 10 grams of the diluted solution (5% by weight in an aqueous solution) of (trimethoxysilyl)propyldimethyl-octadecylammonium chloride,
the filler 2' is obtained under the same conditions as for the filler 1' but by reaction, in a fluidized bed, between 30 grams of amorphous silica Cab-O-Sil M5® and 5 grams of the 5% aqueous (trimethoxysilyl)-propyldimethyloctadecylammonium chloride solution,
the filler 3' is obtained under the same conditions as for the filler 1' but by reaction, in a fluidized bed, between 30 grams of amorphous silica Cab-O-Sil M5® and 3 grams of the 5% aqueous (trimethoxysilyl)-propyldimethyloctadecylammonium chloride solution.

The procedure for producing the products otherwise remains identical to that described above in connection with examples 1 to 9.

The proportions by weight (base 100 for the silicone base) of the various constituents used for the ten examples carried out are combined in table 5 below.

TABLE 5

|  | Ex. 10 | Ex. 11 | Ex. 12 | Ex. 13 | Ex. 14 | Ex. 15 | Ex. 16 | Ex. 17 |
|---|---|---|---|---|---|---|---|---|
| Silicone base | 100 | 100 | 100 | 100 | 100 | 100 | 100 | 100 |
| Perkadox Pd 50s | 1.25 | 1.25 | 1.25 | 1.25 | 1.25 | 1.3 | 1.25 | 1.25 |

TABLE 5-continued

|          | Ex. 10 | Ex. 11 | Ex. 12 | Ex. 13 | Ex. 14 | Ex. 15 | Ex. 16 | Ex. 17 |
|----------|--------|--------|--------|--------|--------|--------|--------|--------|
| Filler 2'| 2      | 5      | 10     | —      | —      | —      | —      | —      |
| Filler 1'| —      | —      | —      | 2      | 5      | —      | —      | —      |
| Filler 3'| —      | —      | —      | —      | —      | 2      | 5      | 10     |

The biocidal activity of Ex. 10 to 17 was determined according to standard JIS Z 2801-2000 described above, the bacterial strain used being *Escherichia coli*, according to a method identical to that described above.

The results obtained for the products according to examples 10 to 17, by comparison with the blank (without product) and the control product (without filler), are summarized in table 6.

TABLE 6

| Example | Filler | Filler/matrix (% by weight) | Alkylsil./matrix (% by weight) | $Log_{10}$ CFU | $Log_{10}$ CFU reduction | Activity (%) |
|---------|--------|---------|---------|-------|---------|---------|
| Blank   | —      | —       | —       | 5.87  | —       | —       |
| Control | none   | 0       | 0       | 4.81  | 1.06    | —       |
| Ex. 10  | 2'     | 2       | 0.014   | 0.00  | 5.87    | >99.9   |
| Ex. 11  | 2'     | 5       | 0.036   | 0.00  | 5.87    | >99.9   |
| Ex. 12  | 2'     | 10      | 0.072   | 0.00  | 5.87    | >99.9   |
| Ex. 13  | 1'     | 2       | 0.025   | 0.00  | 5.87    | >99.9   |
| Ex. 14  | 1'     | 5       | 0.063   | 0.00  | 5.87    | >99.9   |
| Ex. 15  | 3'     | 2       | 0.009   | 0.00  | 5.87    | >99.9   |
| Ex. 16  | 3'     | 5       | 0.023   | 0.00  | 5.87    | >99.9   |
| Ex. 17  | 3'     | 10      | 0.045   | 0.00  | 5.87    | >99.9   |

It is seen, from the results given in table 6, that all the products obtained according to the invention make it possible to reduce *E. coli* bacterial growth in a proportion of approximately 100%, thus demonstrating a very high biocidal activity of the systems according to the invention, even for extremely low amounts of the biocidal active agent, that is to say of the alkylsilane.

Surprisingly, it is thus noticed that a very low proportion, of the order of 0.01%, of the alkylsilane biocidal agent comprising a quaternary amine functional group with respect to the matrix, indeed even less, results, however, in a high antibacterial activity of the product. Such a property also advantageously makes it possible to minimize the amount of biocidal agent introduced into the product and results, in the end, in the minimizing of the risk, over time, of "sweating" of said agent at the surface of the material and into the external environment.

G—Comparative Examples

Attempts have also been made to show, through other comparative examples, the superiority of the products according to the invention.

In the following comparative examples 25 to 27, the biocidal agent of alkylsilane type was introduced into the matrix using a carrier material. This carrier material is obtained by means of a wax of the glycol copolymer type.

More specifically, the comparative samples were obtained according to the following experimental protocol:

In a first step, the carrier material, composed of a mixture of the biocidal agent of alkylsilane type, the remainder being a glycol copolymer, in a 50/50 proportion, is synthesized.

Subsequently, the comparative sample is synthesized by incorporating the comparative filler, composed of the wax and the biocidal agent, in the silicone elastomer matrix sold by Rhodia Silicone under the reference Rhodorsil MF 960 U. As for the preceding examples, the silicone base is vulcanized by the use of a product sold under the reference Perkadox PD 50s®, the vulcanizing agent of which is di(2,4-dichlorobenzoyl) peroxide, according to the protocol described in the preceding part D.

The characteristics of the samples thus obtained, by comparison with another series of samples according to the invention synthesized in parallel using the same fillers 2' and 1' as described above, are summarized in table 7 below. The biocidal activity of all the samples (examples 19 to 27 below) was evaluated according to the principles and protocols described above in part E.

TABLE 7

| Example | Filler (carrier) | Filler (carrier)/matrix (% by weight) | Alkylsil./matrix (% by weight) | $Log_{10}$ CFU | $Log_{10}$ CFU reduction | Activity (%) |
|---------|------------------|--------|--------|------|------|--------|
| Blank   | —                | —      | —      | 3.59 | —    | —      |
| Ex. 19  | 2'               | 2      | 0.014  | 0.00 | 3.59 | >99.9  |
| Ex. 20  | 2'               | 1.27   | 0.009  | 0.00 | 3.59 | >99.9  |
| Ex. 21  | 2'               | 0.97   | 0.007  | 0.00 | 3.59 | >99.9  |
| Ex. 22  | 1'               | 1.14   | 0.014  | 0.00 | 3.59 | >99.9  |
| Ex. 23  | 1'               | 0.73   | 0.009  | 0.00 | 3.59 | >99.9  |
| Ex. 24  | 1'               | 0.56   | 0.007  | 0.00 | 3.59 | >99.9  |
| Ex. 25  | (wax)            | 0.41   | 0.206  | 0.00 | 3.59 | >99.9  |
| Ex. 26  | (wax)            | 0.26   | 0.131  | 0.00 | 3.59 | >99.9  |
| Ex. 27  | (wax)            | 0.20   | 0.100  | 1.77 | 1.82 | 98.5   |

It is seen, by comparison with examples 19 to 24 according to the invention, that the biocidal activity of comparative examples 25 to 27 is much lower than that obtained above for the samples according to the invention, for an identical level of concentration of the agent in the matrix. In particular, when the biocidal agent of the alkylsilane type is introduced without filler into the matrix, the maximum effectiveness can be obtained only for levels of biocidal agent of greater than 0.1% by weight in the matrix. In contrast, the use of a filler according to the invention makes it possible to obtain a maximum activity for proportions of biocidal agent in the matrix which are 10 times lower or even 15 times lower.

Such a difference indicates the importance of the mineral filler of silica type to which the molecules of the biocidal agent are grafted. Very unexpectedly, such an implementation makes it possible to greatly reduce the level of biocidal agent necessary to obtain a maximum activity of the final product.

In particular, it is also possible to greatly reduce, by such a grafting, the risks that a portion, even a minimum portion, of the biocidal agent will "sweat" through the material and be discharged into the external environment, for example into a liquid circulating through a food tube.

It has also been demonstrated in the context of the present invention, through other additional examples, that the incorporation of the silica fillers alone into the matrix does not result in any specific improvement in the biocidal activity of the material thus obtained.

What is claimed is:

1. An antimicrobial product, comprising a silicone-comprising system, said system comprising:
    a silicone elastomer matrix; and
    a mineral filler of particles selected from the group consisting of a silica and an aluminosilicate,
    wherein said particles are dispersed in said matrix and comprise, grafted to their surface, at least one alkylsilane molecule comprising at least one quaternary ammonium functional group, and
    wherein the product exhibits biocidal activity on its surface.
    wherein the product exhibits biocidal activity on its surface,
    wherein the product is suitable for a food application, and
    wherein a percentage by weight of a total amount of the at least one alkylsilane molecule with respect to the silicone elastomer matrix is greater than 0% and less than 0.2%, thereby providing the biocidal activity.

2. The product of claim 1, wherein the at least one alkylsilane molecule is obtained from at least one precursor of a structure:

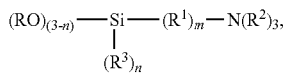

wherein:
m is an integer varying between 1 inclusive and 10 inclusive;
n is 0, 1, or 2;
R is a linear $CH_3$—$(CH_2)_w$ alkyl chain, wherein w is between 0 and 5, or an isomeric branched form of said linear $CH_3$—$(CH_2)_w$ chain;
$R^1$ is a hydrocarbon chain optionally comprising at least one alcohol and/or ether functional group;
the $R^2$ groups, which are identical or different on the same precursor, each represent a linear $(CH_2)_z$—$CH_3$ alkyl chain, wherein z is between 1 and 30, or an isomeric branched form of said linear $(CH_2)_z$—$CH_3$ chain; and
$R^3$ is a second linear $CH_3$—$(CH_2)_w$ alkyl chain, wherein w is between 0 and 5, an isomeric branched form of said second linear $CH_3$—$(CH_2)_w$ chain, or another alkylsilane group.

3. The product of claim 2, wherein:
m=1;
n=0;
w=0, 1, or 2; and
$R^1$ represents a linear $(CH_2)_y$ alkyl, wherein y is between 1 and 10, or an isomeric branched form of said linear $(CH_2)_y$ alkyl.

4. The product of claim 2, wherein the at least one alkylsilane molecule is obtained from a precursor of formula:

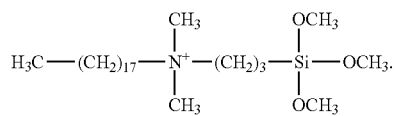

5. The product of claim 1, wherein a mean size of the particles of the mineral filler is between 0.01 micron and 500 microns.

6. The product of claim 1, wherein said particles comprise an amorphous material, a specific surface of which is between 10 and 1000 $m^2/g$.

7. The product of claim 1, wherein the percentage by weight of a total amount of the at least one alkylsilane molecule with respect to the silicone elastomer matrix is greater than 0.005% and less than 0.2%.

8. The product of claim 1, wherein the percentage by weight of a total amount of the at least one alkylsilane molecule with respect to the silicone elastomer matrix is between 0.01% and 0.2%.

9. The product of claim 1, wherein a ratio by weight of the mineral filler grafted with the at least one alkylsilane molecule to the silicone elastomer matrix is between 0.1% and 50%.

10. A silicone elastomer tube comprising the antimicrobial product of claim 1.

11. The product of claim 1, wherein the mineral filler is a zeolite or bentonite.

12. The product of claim 2, wherein w is between 1 and 5.

13. The product of claim 2, wherein for at least one of the $R^2$ groups, z is greater than 15.

14. The product of claim 1, wherein a mean size of the particles of the mineral filler is between 0.1 micron and 200 microns.

15. The product of claim 6, wherein the amorphous material is amorphous silica.

16. The product of claim 6, wherein the specific surface of the particles is between 50 and 500 $m^2/g$.

17. The product of claim 15, wherein the specific surface of the particles is between 50 and 500 $m^2/g$.

18. The product of claim 1, wherein a ratio by weight of the mineral filler grafted with the at least one alkylsilane molecule to the silicone elastomer matrix is between 0.5% and 20%.

19. The product of claim 1, wherein the product is suitable for delivering a liquid food.

20. A method of delivering a liquid food, the method comprising delivering the liquid food with the silicone elastomer tube of claim 10.

* * * * *